United States Patent [19]

Perman et al.

[11] Patent Number: 5,340,614
[45] Date of Patent: Aug. 23, 1994

[54] METHODS OF POLYMER IMPREGNATION

[75] Inventors: Craig A. Perman, Woodbury; Manfred E. Riechert, Maplewood, both of Minn.

[73] Assignee: Minnesota Mining and Manufacturing Company, St. Paul, Minn.

[21] Appl. No.: 16,603

[22] Filed: Feb. 11, 1993

[51] Int. Cl.⁵ .............................................. B05D 3/04
[52] U.S. Cl. .................... 427/2.24; 427/2.25; 427/2.28; 427/2.3; 427/430.1
[58] Field of Search ................ 427/430.1, 2

[56] References Cited

U.S. PATENT DOCUMENTS

| | | | |
|---|---|---|---|
| 3,773,919 | 11/1973 | Boswell et al. | 424/19 |
| 4,167,589 | 9/1979 | Vitzthum et al. | 426/312 |
| 4,598,006 | 7/1986 | Sand | 424/81 |
| 4,678,684 | 7/1987 | Sand | 427/213.36 |
| 4,820,752 | 4/1989 | Berens et al. | 523/340 |
| 4,992,308 | 2/1991 | Sunol | 427/297 |
| 5,043,280 | 8/1991 | Fischer et al. | 435/235 |
| 5,094,892 | 3/1992 | Kayihan | 427/440 |
| 5,169,687 | 12/1992 | Sunol | 427/297 |
| 5,183,663 | 2/1993 | Greiner | 424/443 |

FOREIGN PATENT DOCUMENTS

| | | |
|---|---|---|
| 57091/86 | 3/1986 | Australia . |
| 0200197 | 11/1986 | European Pat. Off. . |
| 0222207 | 5/1987 | European Pat. Off. . |
| 0401713 | 12/1990 | European Pat. Off. . |
| 0405284 | 1/1991 | European Pat. Off. . |

OTHER PUBLICATIONS

Minolta Chroma Meter CR-200/CR231 Technical Reference Manual, Version 2.0, Minolta, Inc., Japan, undated.
Jae-Jin Shim et al; J. Phys. Chem. 1991, vol. 95, 353–360, no months available.
Alan R. Berens et al; J. Applied Polymer Science, 1992, vol. 46, 231–242, no months available.
Jae-Jin Shim et al; AICHE Journal 1989, vol. 35(7), 1097–1106, no months available.
A. R. Berens et al; Supercritical Fluid Science and Technology, ACS Symposium Series, 1989, vol. 406, 207–223, no months available.

*Primary Examiner*—Terry J. Owens
*Assistant Examiner*—Erma Cameron
*Attorney, Agent, or Firm*—Gary L. Griswold; Walter N. Kirn; Carolyn V. Peters

[57] ABSTRACT

Methods of impregnating various polymer substrates with an impregnation additive, by simultaneously contacting the polymer substrate with an impregnation additive, carrier liquid, and supercritical fluid are provided. The impregnation additive is substantially insoluble in the supercritical fluid, and the carrier liquid is preferably substantially insoluble in the supercritical fluid.

19 Claims, 1 Drawing Sheet

METHODS OF POLYMER IMPREGNATION

FIELD OF THE INVENTION

This invention relates to methods of impregnating polymeric materials with additives utilizing supercritical fluids.

BACKGROUND OF THE INVENTION

A variety of methodologies have been employed in an attempt to impregnate polymers, and in particular thermoplastic polymers, with various impregnation additives. For example, certain polymers can be impregnated with selected additives by immersing the polymers in a solution comprised of the additives for an extended period of time. In addition, it may also be possible to incorporate the additives into polymers during melt processing and/or extrusion. Furthermore, additives may be impregnated into polymers by dissolving the additives into various compounds, such as $CO_2$, $N_2O$, and ethylene, maintained at or near their supercritical temperatures and pressures, and contacting this mixture with the polymer or polymers to be impregnated. Above a defined temperature and pressure, these pressurized compounds form supercritical fluids that serve both as swelling agents for the polymers to be impregnated, and as volatile solvents for additives to be impregnated into the polymers.

Existing methods of impregnating polymers with additives using supercritical fluids are limited by the requirement that the selected additive or additives be soluble in the supercritical fluid, and that the mixture of the additive solubilized in the supercritical fluid be compatible with (i.e. soluble in) the polymer to be impregnated. For example, U.S. Pat. No. 4,598,006 (Sand) discloses a method for impregnating a thermoplastic polymer with an impregnation material (i.e. a fragrance, a pest control agent, or a pharmaceutical composition) by dissolving the impregnation material in a volatile swelling agent (e.g., $CO_2$ maintained at or near supercritical conditions, swelling the thermoplastic polymer by contacting it with the supercritical or nearly supercritical volatile swelling agent containing the impregnation material, and reducing the pressure so the volatile swelling agent diffuses out of the thermoplastic polymer. Among other limitations, Sand teaches that the impregnation material must be soluble in the volatile swelling agent, and that the volatile swelling agent be compatible with (i.e. soluble in) the polymer to be impregnated. Given the lipophilic nature to the volatile swelling agents and polymers disclosed in Sand, the impregnation materials disclosed in Sand are also lipophilic. See also, U.S. Pat. No. 4,678,684; EPO Patent Application Nos. 0 200 197, 0 401 713, 0 405 284; and Australian Patent Application No. 57091/86.

Similarly, U.S. Pat. No. 4,820,752 (Berens et al.) discloses a process for infusing an additive into a polymer by dissolving the additive into a compressed normally gaseous fluid solvent (e.g., $CO_2$) that has a boiling point below room temperature and a density of at least 0.01 g/cc, contacting the solution of the additive and normally gaseous fluid solvent with a polymeric material for a time sufficient to allow at least part of the solution to be absorbed into the polymeric material, and separating the normally gaseous fluid Bolvent from the polymeric material leaving the additive infused within the polymeric material. Importantly, Berens et al. discloses that the additive must have some degree of solubility in the compressed fluid, and the solution of the compressed fluid and additive must have some degree of solubility in the polymeric material. See also, EPO Patent Application No. 0 222 207.

In addition, supercritical fluids have also been used as a solvent to re-impregnate aromatic components into a tea residue after the caffeine component of the tea had been extracted (U.S. Pat. No. 4,167,589; Vitzthum et al.), as a solvent during the preparation of substance embedded microspheres, by dissolving a substance and polymeric carrier, with or without a liquid medium, into a supercritical gas (U.S. Pat. No. 5,043,280; Fisher et al.), and as a solvent for various monomers or polymers to be impregnated into porous materials, such as wood, to increase the strength and other properties of the porous materials (U.S. Pat. Nos. 4,992,308 and 5,169,687; Sunol).

None of the previously disclosed methods can be used to successfully impregnate additives, and in particular hydrophilic additives, into polymers when the additives are incompatible with (i.e. substantially insoluble in) the supercritical fluid. In fact, to date, no method has been provided for the impregnation of additives into polymers when such additives are substantially insoluble in the supercritical fluid.

SUMMARY OF THE INVENTION

Surprisingly, it has been discovered that impregnation additives that are substantially insoluble in a supercritical fluid can be impregnated into polymer substrates by simultaneously contacting the polymer substrate with the impregnation additive and a carrier liquid, such as water, in the presence of the supercritical fluid. Even more surprisingly, such impregnation can be accomplished using impregnation additives that are incompatible with (i.e. insoluble in) the polymer substrate, and using carrier liquids that are substantially insoluble in the supercritical fluid and/or are incompatible with (i.e. insoluble in) the polymer substrate.

In particular, the present invention provides a method of impregnating a polymeric material with an impregnation additive by simultaneously contacting a polymeric material with a carrier liquid and an impregnation additive, exposing the polymeric material, carrier liquid and impregnation additive to a supercritical fluid in a pressure vessel for sufficient time to swell the polymeric material, such that the carrier liquid and impregnation additive can at least partially penetrate the polymeric material, and releasing the pressure in the pressure vessel so that the carrier liquid diffuses out of the polymeric material, thereby entrapping an amount of the impregnation additive within the polymeric material, wherein the impregnation additive is substantially insoluble in supercritical fluid.

In addition, the present invention also provides a method of impregnating a polymeric material with a hydrophilic impregnation additive by simultaneously contacting a polymeric material with a carrier liquid and a hydrophilic impregnation additive, exposing the polymeric material, carrier liquid and hydrophilic impregnation additive to a lipophilic supercritical fluid in a pressure vessel for sufficient time to swell the polymeric material, such that the carrier liquid and hydrophilic impregnation additive can at least partially penetrate the polymeric material, and releasing the pressure in the pressure vessel so that the carrier liquid diffuses out of the polymeric material, thereby entrapping an amount of the hydrophilic impregnation additive within the polymeric material.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWING

The invention may be further illustrated by reference to the accompanying Drawings wherein.

DETAILED DESCRIPTION OF EMBODIMENTS OF THE INVENTION

General Method

Figure 1:
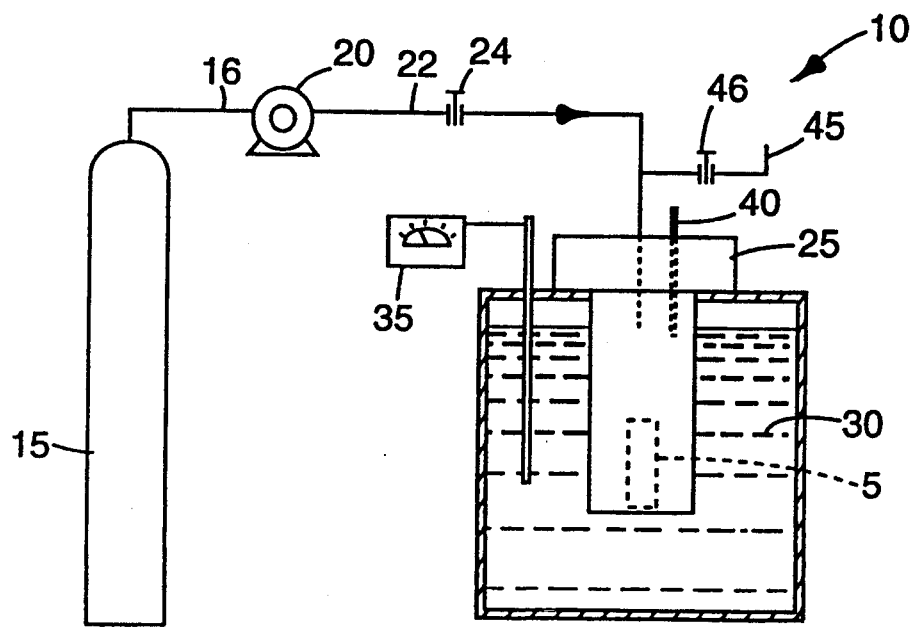
FIG. 1 is a schematic illustration (not to scale) of an impregnation apparatus for impregnating polymers with selective impregnation additives according to the methods of the present invention.

FIG. 1 schematically illustrates an impregnation apparatus 10 for the impregnation of polymers with selected impregnation additives according to the methods of the present invention. The major components of the impregnation apparatus 10, include a tank 15 that holds the material to be used as a supercritical fluid, a compressor 20 to pressurize and transfer the supercritical fluid from the tank 15 to a pressure vessel 25, a water or oil bath 30 in which the pressure vessel 25 is suspended, a temperature regulator 35 to maintain the water/oil bath 30 at a predetermined temperature, a pressure transducer 40 to monitor and maintain the pressure within the pressure vessel 25 at a predetermined level, and a vent line 45, to be used to vent the supercritical fluid from the pressure vessel 25 after impregnation of a polymer has been accomplished.

In use, a polymer sample to be impregnated (not shown) is placed in a container 5, such as a beaker or test tube, within the pressure vessel 25. The polymer sample is covered with a solution of a carrier liquid and one or more impregnation additives (not shown), and maintained completely submerged in this solution via a glass wool plug or other inert material placed in the top of the container 5. The pressure vessel 25 is then sealed, and placed or maintained in water/oil bath 30.

To start the impregnation process, a selected material, such as carbon dioxide, is transferred from tank 15 via line 16 to compressor 20, where it is pressurized to the critical pressure ($P_c$) of the material, or greater. The compressed material leaves compressor 20 via line 22 and valve 24, and is transferred into the pressure vessel 25 containing the polymer sample to be impregnated, after which valve 24 is closed.

When the pressurized material enters pressure vessel 25, it may already comprise a supercritical fluid, so long as the temperature of the pressurized material exceeds the critical temperature ($T_c$) of the material. However, if the pressurized material has not yet reached or exceeded $T_c$, then water/oil bath 30 can be heated using temperature regulator 35 to rapidly convert the pressurized material into a supercritical fluid capable of swelling the polymer sample according to the methods of the present invention. In this regard, it will be appreciated that both temperature regulator 35 and pressure transducer 40 can be used to maintain pressure vessel 25, including the supercritical fluid, polymer sample, impregnation additive, and carrier liquid contained therein, at a preselected temperature and pressure above the $T_c$ and $P_c$ of the supercritical fluid.

After sufficient time has passed to complete impregnation of an impregnation additive into the polymer sample in container 5, the supercritical fluid contained in pressure vessel 25 is vented from the pressure vessel 25 via vent line 45 by keeping valve 24 closed, and opening valve 46. In this regard, pressure vessel 25 should be vented in a controlled manner (e.g., at a slow regular rate) to prevent damage (e.g., fracturing and/or foaming) to the polymer samples.

It will be appreciated that vent line 45 may be vented directly to the atmosphere, or may be vented into a holding container (not shown), re-circulated to tank 15, as need be. After the supercritical fluid has been vented, pressure vessel 25 can be opened, and the impregnated polymer sample recovered from container 5.

While the impregnation of a polymer sample with one or more impregnation additives according to the methods of the present invention has been illustrated with respect to FIG. 1, it will be appreciated that any apparatus capable of containing a supercritical fluid, polymer sample, carrier liquid, and impregnation additive(s), such that the polymer sample is impregnated with the impregnation additive(s), is considered to fall within the scope of the present invention. In this regard, those skilled in the art will be readily capable of adapting the apparatus illustrated in FIG. 1, such as through the incorporation of a thermocouple into pressure vessel 25, thereby eliminating the need for water/oil bath 30, or in any other manner consistent with the practice of the methods of the present invention.

Supercritical Fluid

As used herein, a supercritical fluid refers to a material maintained at or above its critical temperature ($T_c$) and critical pressure ($P_c$) (i.e. above its critical point ($C_p$)), so as to place the material in a supercritical fluid state. Typically, supercritical fluids are gases at ambient temperature (approximately 22° C.) and pressure (approximately 1.01 mega Pascals (MPa)). However, when maintained at or above $C_p$, the supercritical fluid displays properties of both a gas and a liquid. In particular, such a supercritical fluid has the solvent characteristics of a liquid, but the low surface tension of a gas. Accordingly, as with a gas, the supercritical fluid can more readily diffuse into a selected solute material, such as a polymer.

Figure 2:
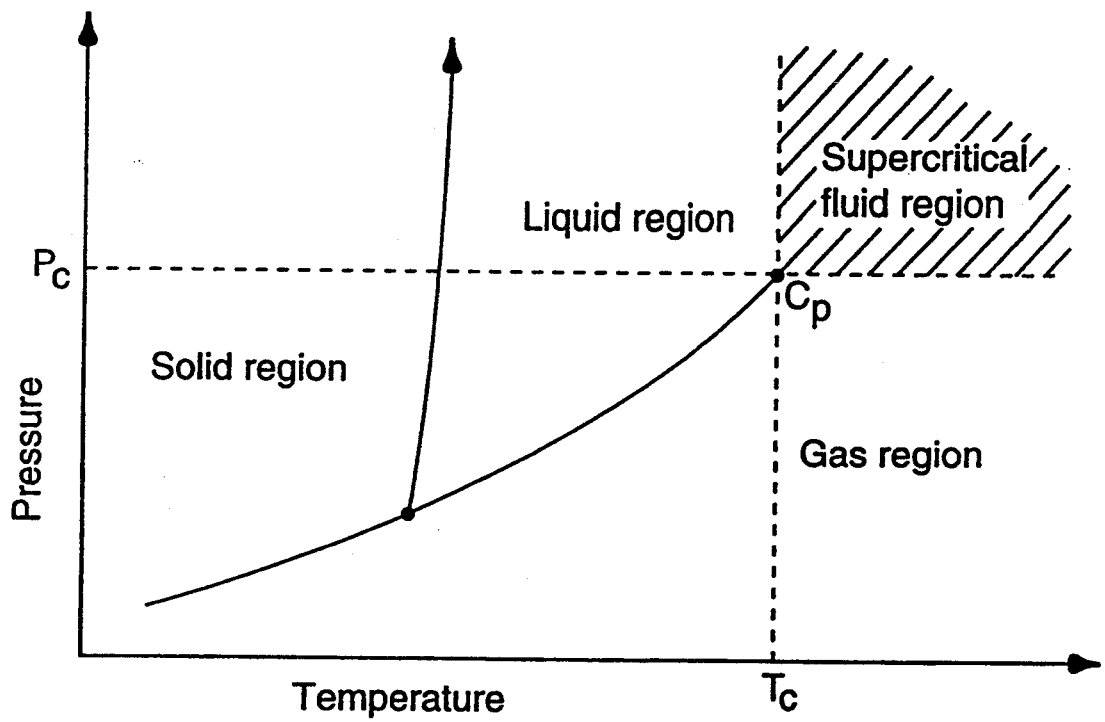
FIG. 2 is a diagram illustrating the various states of matter of a material capable of forming a supercritical fluid useful in the method of the present invention.

FIG. 2 diagrammatically illustrates the various states of matter of a typical material capable of forming a supercritical fluid. At appropriate temperatures and pressures the selected material may take the form of a solid, a liquid, or a gas. However, above a defined $T_c$ and $P_c$, the material takes the form of a supercritical fluid displaying the properties noted above. Thus, the supercritical fluid region for such a material is defined by the shaded region of FIG. 2, encompassing all temperatures and pressures beyond the $C_p$ of the material.

Table 1 lists several nonlimiting examples or supercritical fluids, including their critical temperatures and pressures, that are useful in the methods of the present invention.

TABLE 1

Critical temperatures ($T_c$) and critical pressures ($P_c$) of selected supercritical fluids.

| Supercritical Fluid | $T_c$ in °C. | $P_c$ in MPa |
|---|---|---|
| carbon dioxide | 31.1 | 7.38 |
| nitrous oxide | 36.5 | 7.26 |
| ethylene | 9.3 | 5.03 |
| ethane | 32.3 | 4.88 |
| chlorotrifluoromethane | 29.9 | 3.92 |

In addition to the supercritical fluids listed in Table 1, a large number of other materials are also useful in the methods of the present invention, including without limitation, nitrogen, propane, propylene, cyclohexane, isopropanol, benzene, toluene, p-xylene, ammonia, water, methane, trichlorofluoromethane, tetrafluoroethylene, perfluoroethane, tetrafluoromethane, trifluoromethane, and 1,1 difluoroethylene. The specific $T_c$ and $P_c$ for each of these materials, and for any other supercritical fluid useful in the methods of the present invention, are readily obtainable in a number of standard references, including the *CRC Handbook of Chemistry and Physics*, 67th ed., CRC Press Inc., Boca Raton, Fla., 1987, *Matheson Gas bata Book*, 6th ed., Matheson Co., Inc., Lyndhurst, N.J., 1980, *Merck Index*, 10th ed., Merck and Co., Rahway, N.J., 1983, and *Lange's Handbook of Chemistry*, 12th ed., McGraw Hill Book Co., New York, N.Y., 1979, the disclosures of which are herein incorporated by reference. Furthermore, it is also contemplated that mixtures of two or more supercritical fluids could also be used in the methods of the present invention.

While any of a variety of supercritical fluids are useful in the methods of the present invention, it is preferred that the supercritical fluid be substantially nonreactive and nontoxic (i.e. inert) with respect to the impregnation additives, carrier liquids, and polymers used in the methods of the present invention. In fact, the relative inertness of the supercritical fluid used in the methods of the present invention is particularly important with many of the biologically active additives impregnated into polymers according to the methods of the present invention. For example, when impregnating an active polypeptide (e.g. insulin) into a polymer substrate, a reactive supercritical fluid could inhibit or completely destroy the desired biological activity of such a polypeptide. Likewise, a toxic supercritical fluid may remain as a residual additive within the polymer substrate along with the impregnated polypeptide. Under either or both scenarios, the usefulness of impregnating such a polypeptide additive into a polymer substrate would be compromised or lost.

Other factors that can influence the selection of a supercritical fluid for use in the methods of the present invention include cost of the supercritical material, solubility of the supercritical material in the polymer to be impregnated and the carrier liquid, as well as the practical working limits of the $T_c$ and $P_c$ of the supercritical fluid. In this regard, it is preferred that the $T_c$ of the supercritical fluid be as close as possible to ambient conditions (e.g. approximately 22° C.), such that the supercritical fluid can be maintained at a temperature of from about 0° C. to about 100° C., preferably from about 20° C. to about 90° C., and most preferably from about 30° C. to about 80° C. These Preferred temperature limits will prove particularly important with respect to biologically active additives, such as the active polypeptides noted above, which can be particularly susceptible to thermal degradation at temperatures in excess of about 40° C.

The preferred limits on the PC and the operating pressures of the supercritical fluid used in the methods of the present invention are practical in nature. For example, the upper limits of the operating pressures will be dictated, among other things, by the cost and availability of equipment capable of containing pressures in excess of 138 MPa (20,000 psi), as well as the susceptibility of the impregnation additive and/or polymer to degradation at higher pressures. In this regard, it is preferred that the supercritical fluid be maintained at pressures from about 4 MPa to about 138 MPa, preferably from about 5 MPa to about 45 MPa, and most preferably from about 7 MPa to about 30 MPa. with the preferred temperature limitations noted above, biologically active additives will preferably be subjected to the minimum critical pressures necessary to ensure impregnation according to the methods of the present invention.

With respect to the solubility of the supercritical fluid in the polymer or polymers to be impregnated by the methods of the present invention, it is preferred that the selected supercritical fluid show minimal solubility in the polymer to be impregnated. Thus, the supercritical fluid should have sufficient solubility to swell the polymer matrix, and thereby allow for the penetration of the carrier liquid and impregnation additive therein, but not provide such a degree of solubility that the polymer matrix loses its form and/or dissolves substantially into the supercritical fluid.

Given the requirements outlined above, supercritical carbon dioxide provides a particularly preferred supercritical fluid for use in the methods of the present invention. Supercritical carbon dioxide is a low cost, inert, material displaying a $T_c$ of 31.1° C. and a $P_c$ of 7.38 MPa. Furthermore, supercritical carbon dioxide displays sufficient solubility to swell a wide variety of polymeric materials, including both homopolymers and copolymers, such as polyethylene, polypropylene, polyamide, polyurethane, silicone, albumin, lactic acid polymers, and glycolic acid polymers, without dissolving or otherwise dissociating the polymer matrix.

Impregnation additives

The impregnation additive can comprise any element, compound or composition capable of being impregnated into a polymer using a supercritical fluid and a carrier liquid according to the present invention, so long as the impregnation additive is substantially insoluble in the supercritical fluid. As used herein, an impregnation additive is substantially insoluble in a supercritical fluid when none or virtually none of the impregnation additive will dissolve into the supercritical fluid at a predetermined temperature and pressure above the $C_p$ of the supercritical fluid. In this regard, an impregnation additive will be considered to be substantially insoluble in a supercritical fluid, so long as no more than an insignificant quantity, not readily detected by conventional means, dissolves into the supercritical fluid.

Nonlimiting classes of impregnation additives useful in the methods of the present invention include dyes, monomers, drugs, proteins, polypeptides, nucleotides, and combinations thereof. Preferably, the impregnation additive will comprise a biologically active drug, polypeptide, or protein, including enzymes, hormones, antibiotics, anti-inflammatory agents, analgesics, calcium channel blockers, beta-blockers, antidepressants, antacids, antidiabetics, cerebral stimulants, sedatives, antiparasitics, decongestants, muscle relaxants, anti-Parkinsonism agents, antiviral agents, bronchodilators, vitamins and dietary supplements and the like. Nonlimiting examples of suitable polypeptides and proteins useful as impregnation additives in the methods of the present invention include immunomodulators such as Thymic Humoral Factor, growth Factors such as Human Growth Factor and Fibroblast Growth Factor, antitumorals such as BCNU and epirubian, hormones such as LHRH, and steroidals such as medroxyprogesterone acetate and magestrol acetate.

In an alternative embodiment of the present invention, the impregnation additive comprises one or more monomers, such as acrylic acid, ethylene, or propylene. In this embodiment, a polymer substrate undergoes a series of impregnations with one or more monomers followed by a polymerization of such monomers in situ to increase the strength, modulus, or other properties of the polymer substrate.

Preferably, the impregnation additive according to the present invention is substantially insoluble over the entire critical temperature and pressure ranges of the supercritical fluid used in the methods of the present invention. However, it is to be understood that the impregnation additive need only be substantially insoluble in a supercritical fluid maintained at a set temperature and pressure to be considered within the scope of the present invention.

One method of determining the insolubility of an impregnation additive in a supercritical fluid is to compare the solubility parameter of the impregnation additive with that of the supercritical fluid at a set temperature and pressure, or over a temperature and pressure range. When the solubility parameter for a solvent and a solute are within about 1 $(cal/cc)^{\frac{1}{2}}$, then complete miscibility between the solvent and solute will generally occur. As the difference between the solubility parameters of the solvent and solute increase, the solute will becoming increasingly less soluble in the solvent, until a point is reached where the solute is substantially insoluble in the selected solvent.

The solubility parameters of most materials are readily available and/or determinable by those skilled in the art. In this regard, such parameters can typically be found in a number of standard references, including Volume 21 of the *Encyc. of Chemical Technology*, 3rd ed., Wiley & Sons, New York, N.Y., pp. 377–401, 1984, the disclosures of which are herein incorporated by reference. Even when such parameters are not available in a standard reference, they can be estimated using standard equations for solubility parameters, such as Gaddings equations. For a more through discussion of solution chemistry and estimation of solubility parameters, reference should be had to Volume 21 of the *Encyc. of Chem. Tech.* and the *Encyc. of Polymer Science and Engineering*, Vol. 15, pp 380–402, 1989, the disclosures of which are herein incorporated by reference.

Even when the solubility parameters of an impregnation additive and/or supercritical fluid cannot be readily obtained, the solubility, or lack thereof, of the impregnation additive in the supercritical fluid can be determined by a simple series of tests utilizing an apparatus, such as the impregnation apparatus illustrated in FIG. 1 herein. Specifically, in a first test, the impregnation additive and polymer to be impregnated can be placed in separate open containers 5 and 5' (not shown) inside of pressure vessel 25, which is then charged with the selected supercritical fluid at a predetermined temperature and pressure. After a predetermined period of time, typically an hour or more, the pressure vessel 25 is vented via vent line 45, and the polymer and impregnation additive removed.

At the same or different time, in a second test, the impregnation additive and polymer should be simultaneously contacted with a carrier liquid in pressure vessel 25 using the same supercritical fluid and conditions according to the method of the present invention. Thereafter, the pressure vessel 25 is vented via vent line 45, and the polymer removed.

Both polymer samples can then be visualized or otherwise assayed by means well known to those skilled in the art to determine whether or not the impregnation additive impregnated the polymer sample. If the polymer sample subjected to the method of the present invention shows impregnation, but the polymer sample maintained in separate containers does not, then it can be concluded that the impregnation additive was insoluble in the supercritical fluid at the selected conditions, and accordingly, that only the method of the present invention can provide for the impregnation of the polymer with the impregnation additive at the given temperature and pressure conditions.

Carrier liquids

The carrier liquid used in the method of the present invention is normally a liquid at atmospheric pressures and room temperature, and will typically remain a liquid during contact with the supercritical fluid. Preferably, the carrier liquid should be capable of partially or completely dissolving (i.e., forming a solution with) the impregnation additive to be impregnated into a polymer substrate according to the methods of the present invention. However, solubility of the impregnation additive into the carrier liquid is not required to practice the method of the present invention. Thus, in addition to true ionic or molecular solutions of the carrier liquid and impregnation additive, colloidal suspensions and two-phase dispersions of the impregnation additive and carrier liquid are also considered to fall within the scope of the methods of the present invention.

As with the selected supercritical fluid, the carrier liquid will preferably be low cost, and inert (i.e. nonreactive and nontoxic) with respect to the impregnation additive, polymer substrate, and supercritical fluid. In addition, the carrier liquid will preferably be substantially insoluble in the polymer to be impregnated, but at the very least, the carrier liquid must not dissolve or otherwise dissociate the polymer substrate to be impregnated. Furthermore, it is also preferable that the carrier liquid does not have a high degree of solubility in the supercritical fluid under the process conditions, as the carrier liquid would then evaporate from the impregnation additive/carrier liquid solution, leaving a dry or nearly dry impregnation additive incapable of forming a solution with the supercritical fluid, and therefor incapable of impregnating the chosen polymer.

Given the above requirements, water is the preferred carrier liquid for use in the methods of the present invention. Water is a low cost, inert liquid, that is poorly soluble or insoluble in most supercritical fluids and polymers to be impregnated. In addition, water is an excellent solvent for a wide variety of ionic compounds, and is readily capable of forming molecular solutions, colloidal suspensions, and various two phase dispersions.

A variety of other carrier liquids may also be used in the methods of the present invention, including, without limitation, methanol, ethanol (ETOH), hexane, and combinations thereof. All of these carrier liquids typically suffer from one or more disadvantages (e.g. toxicity, reactivity, COBT, solubility in the polymer substrate, and/or solubility in the supercritical fluid) with respect to water, that make them less preferred in the methods of the present invention. However, some of these shortcomings may be overcome or diminished by using various mixtures of carrier liquids (e.g a mixture of water and ETOH) as the carrier liquid component in the methods of the present invention.

For example, ETOH can serve as a useful carrier liquid in the methods of the present invention, particularly when the impregnated polymer is being employed in a nonbiological system. In addition to potential toxicity problems, ETOH is also somewhat soluble in typical supercritical fluids, such as supercritical carbon dioxide. Thus, when ETOH is employed as a carrier liquid, excess ETOH should be placed in the pressure vessel, such that a saturated solution of ETOH in the supercritical fluid is formed during processing. By maintaining a saturated environment within the pressure vessel, the polymer to be impregnated will remain immersed in the ETOH/impregnation additive solution throughout processing, thereby ensuring impregnation of the impregnation additive into the polymer substrate.

Polymers

Virtually any swellable polymeric material, including both homopolymers and copolymers, is useable in the methods of the present invention. Nonlimiting examples of polymeric materials useful in the method of the present invention include polyolefins, polyamides, polyimides, polyesters, polyurethanes, polyacrylates, polycarbonates, polyacetylenes, polyisoprene polymers, polystyrenes, styrenebutadiene polymers, chloroprene polymers, polyether-amides, vinyl chloride polymers, vinylidene chloride polymers, natural rubbers, butyl rubbers, nitrile rubbers, silicone, polyvinyl alcohol polymers, cellulobe derivative polymers, protein derivative polymers (e.g., albumin), lactic acid polymers, glycolic acid polymers, and combinations thereof. Preferred polymers include, without limitation, low density polyethylene, linear low density polyethylene, polypropylene, polyamide, polymers, albumin (e.g., BSA), and polymers prepared from lactic acid alone, glycolic acid alone, or lactic acid and glycolic acid copolymers.

Process Parameters and Advantages

While not being held to a theory of operation, it is believed that the method of the present invention functions to impregnate polymer substrates with an impregnation additive in a significantly different manner than that of the prior art. In the prior art methods, the supercritical fluid serves both as a solvent for the additive and as a swelling agent for the polymer to be impregnated. In contrast, in the methods of the present invention, the impregnation additive is substantially insoluble in the supercritical fluid. Therefore, the supercritical fluid acts only to swell the polymer, after which the impregnation additive solubilized in the carrier liquid impregnates or otherwise diffuses into the polymer substrate. Thus, it is believed that only the intimate simultaneous contact of an impregnation additive solubilized in the carrier liquid with the swollen polymer substrate will allow for the impregnation of the impregnation additive into the polymer substrate.

After the impregnation additive and carrier liquid impregnate the swollen polymer substrate, the pressure in the pressure vessel containing the polymer and supercritical fluid is slowly reduced. It is believed that the gradual release of the pressure decreases the swelling of the polymer, thereby entrapping an amount of the impregnation additive within the polymer substrate. For example, when an ionic or molecular solution of a carrier liquid and impregnation additive (the CL/IA solution), impregnate a swollen polymer, the gradual shrinking of the swollen polymer by releasing the pressure in the pressure vessel, resulting in the precipitation or other deposition of the impregnation material from the CL/IA solution, eventually entrapping the impregnation additive within the polymer matrix.

Since the carrier liquid acts to transport the impregnation additive within the polymer matrix, the methods of the present invention should function whether the impregnation additive forms an ionic or molecular solution, a colloidal suspension, or a two phase dispersion with the carrier liquid. With a colloidal suspension or two-phase dispersion, the mixture of the impregnation additive and carrier liquid may require pulsating or continuous agitation during impregnation to ensure that the additive remains essentially evenly dispersed or suspended in the carrier liquid. Absent such agitation, it is believed that an ionic or molecular solution of the impregnation additive in the carrier liquid will be a preferred manner of practicing the method of the present invention.

A number of parameters and characteristics of the selected supercritical fluid, impregnation additive, carrier liquid, and polymer substrate influence the degree to which the impregnation additive impregnates the polymer substrate. For example, three important variables, temperature, pressure, and time, come into play during the impregnation of a polymer substrate by an impregnation additive.

In general, the higher the temperature employed during impregnation, the greater the swelling of the polymer substrate. This in turn has the capacity to increase the amount of impregnation additive entering the polymer substrate. However, as noted above, the ability to use higher impregnation temperatures is tempered, among other things, by the susceptibility to the impregnation additive to thermal degradation. Thus, many biologically active materials, and in particular biologically active polypeptides, are readily subject to thermal degradation. Furthermore, the susceptibility of the polymer substrate to thermal degradation and/or melting will also place a practical limit on the temperatures employed in polymer impregnation.

In a similar fashion, the pressures employed during polymer impregnation are also limited by practical considerations. While increased pressures generally lead to increased swelling of the polymer substrate, a point is reached where the surface pressure exerted by the supercritical fluid at very high pressures may counteract the increased swelling of the polymer substrate, thereby placing a practical cap on the pressures that can or should be employed in such a method. In addition, it is known that many biologically active materials, such as polypeptides, degrade or otherwise lose their activity when exposed to high pressure conditions, particularly over an extended period of time. Accordingly, such materials should be impregnated at as low a pressure as possible, while still staying at or above the $P_c$ of the supercritical fluid being used in the methods of the present invention.

In general, longer periods of exposure to a supercritical fluid at supercritical conditions will favor deeper penetration of an impregnation additive into a polymer substrate. In this regard, the need to utilize relatively long periods of exposure will prove particularly necessary the larger and thicker the polymer substrate to be impregnated. For example, a 3 mm in diameter polyethylene bead, having a relatively large surface area, may require approximately two hours in which to impregnate an aqueous dye solution (e.g. rose bengal dye) to its core, while a 2.5 cm×2.5 cm×0.5 cm thick polyethylene film may require in excess of 6 hours of exposure to the impregnation conditions to achieve the same degree of penetration as the polyethylene bead. However, the total period of exposure to impregnation conditions will always have to be balanced against the degree of degradation of the impregnation additive and/or polymer substrate resulting from prolonged exposure at the chosen temperature and pressure conditions employed.

Several characteristics or properties of the polymer, such as the crystallinity, density, orientation, and amount of crosslinking appear to influence the degree to which any given polymer can be impregnated with an impregnation additive. In general, the higher the density, crystallinity, orientation and crosslinking of the polymer substrate, the more rigorous the conditions needed to successfully impregnate an impregnation additive into a polymer substrate. Thus, a low density, nonoriented polymer that is highly amorphous and non-crosslinked in structure should be relatively easier to impregnate with a given additive than a similar high density, oriented, crystalline polymer with a relatively high degree of crosslinking.

The methods of polymer impregnation of the present invention provide a number of advantages over presently available methods. Principal among these is the ability to impregnate additives which are substantially insoluble in the supercritical fluid swelling agent. To date, existing methods have required the impregnation material to be capable of forming a solution with the supercritical fluid in order to impregnate the impregnation material into a polymer substrate. Thus, only the methods of the present invention can provide for the impregnation of this class of materials into polymer substrates.

The ability of a carrier liquid to transport an impregnation additive into a polymer matrix swollen by exposure to a supercritical fluid provides for the incorporation of incompatible additives and polymer substrates. Thus, hydrophilic impregnation additives, such as rose bengal dye, can be impregnated into hydrophobic polymers such as polyethylene, polypropylene, and polyurethane via the methods of the present invention. In this regard, such hydrophilic impregnation additives could not be impregnated using existing supercritical methods, since these additives are incompatible (i.e., insoluble) with both the lipophilic supercritical fluid (e.g., supercritical $CO_2$) and the hydrophobic polymer substrates. Furthermore, it will also be appreciated that the preferred carrier liquid of the present method is water, which is likewise incompatible with preferred supercritical fluids and hydrophobic polymer substrates.

Though the method of the present invention utilizes impregnation additives that are substantially insoluble in the supercritical fluid, it will be appreciated that the use of carrier liquids according to the present invention could enhance the impregnation of additives with a low degree of solubility in the supercritical fluid. In addition, the method of the present invention may also prove useful to impregnate additives with gaseous mediums, such as $CO_2$, maintained below their $C_p$ (i.e., subcritical). In this regard, as long as the pressurized gaseous medium is capable of swelling the polymer substrate, the intimate simultaneous contact of the impregnation additive, carrier liquid, and swollen polymer substrate should allow the carrier liquid to transport the additive into the polymer matrix, albeit at a somewhat reduced level than would be accomplished using a supercritical fluid.

Use of supercritical $CO_2$ as the preferred supercritical fluid, and water as the preferred carrier liquid will also result in a number of advantages. Both $CO_2$ and water are low cost, inert (e.g., nonreactive and nontoxic) materials, that are easy and safe to work with, and in most instances will have no deleterious effects on either the polymer substrate or impregnation additive.

In addition, water is an excellent solvent or dispersing medium for many impregnation additives, but is substantially insoluble in supercritical $CO_2$ over a wide range of temperature and pressure conditions. Furthermore, the $T_c$ of $CO_2$ is relatively close to ambient conditions, such that a wide variety of biologically active additives can be impregnated into polymer substrates without significantly altering their desired biological activity.

The fact that the impregnation additives of the present invention are substantially insoluble in the supercritical fluids allows for the impregnation of several different additives into polymer substrates at the same time, without unwanted cross-contamination between the various samples. In addition, this same property, in combination with an inert carrier liquid such as water, will allow for complete recovery of often costly unimpregnated additives after the impregnation process is complete. Further, the use of a carrier liquid will, in many cases, prevent the unwanted extraction of various components, such as plasticizers and tackifiers, from the polymer substrates during the impregnation process.

The invention will be further illustrated by reference to the following non-limiting Examples. All parts and percentages are expressed as parts by weight unless otherwise indicated.

EXAMPLES 1 AND 5-10, AND COMPARATIVE EXAMPLES 2-4, AND 11-13

Five gram samples of various polymeric materials were placed in an open glass vial in a 300 cubic centimeter MICRO SERIES ™ pressure vessel (2-9/16 inch outside diameter, 11-¾ inch overall length; Newport Scientific, Inc., Jessup, Md.). The specific polymeric materials utilized included, ASPEN ™ 6806 polyethylene (PE) beads (3 mm diameter; melt index=105° C., linear low density polyethylene; Dow Chemical Co., Midland, Mich.), No. 3145 polypropylene (PP) beads (3 mm diameter; melt index=300° C.; Exxon Chemical Co., Darien, Conn.), and No. 19, 105-1 polyamide pellets (PA) (3 mm diameter; melt index=95° C.; Aldrich Chemical Co., Milwaukee; Wis.). The polymeric materials were contacted with, or remained separate from, an impregnation additive consisting of 0.25 g of rose bengal dye (Aldrich Chemical Co.) in either a dry, powdered form, or in a solution or dispersion of 0.25 g of rose bengal dye in 15 ml of various carrier liquids, including deionized water, hexane, or ethyl alcohol (ETOH). A glass wool plug was used to keep the beads and pellets submerged in the dye/carrier liquid solutions.

After placement of the polymeric material, and dye (with or without a carrier liquid) in the pressure vessel, the vessel was closed and charged with either $CO_2$ or $N_2$ gas. The enclosed system was adjusted to either supercritical or subcritical temperature and pressure conditions for the contained gases (supercritical $CO_2 = 31°$ C. and 7.38 MPa; supercritical $N_2 = -147°$ C. and 3.39 MPa), and maintained at those conditions for 2 hours, after which the pressure vessel was vented down to ambient conditions. The polymeric materials were recovered from the pressure vessel, rinsed with deionized water, allowed to dry at ambient conditions overnight (e.g. 12-18 hrs.), and were observed to determine the degree of dye impregnation into the polymeric materials, if any. The specific combination of polymer material, impregnation additive, carrier medium (if any), supercritical fluid, including temperature and pressures utilized, method of sample treatment, and observed color change (if any), for Examples 1, and 5-10, and Comparative Examples 2-4, and 11-13 are given in Table 2 below.

After visual observation, each of the dried polymer beads were analyzed using a Minolta Chroma Meter No. CR-200/Cr-231 tribtimulus color analyzer to determine the degree of rose bengal dye impregnation, if any. Undyed and untreated polymer beads and pellets were utilized as controls. The Chroma Meter is a compact tristimulus color analyzer for measuring reflective colors of surfaces. Absolute measurements were taken in L*a*b* (CIE 1976) in the Munsell color system. For a more in depth review of the measurement parameters of the Chroma Meter color analyzer, reference should be had to the Minolta Chroma Meter CR-200/CR231 Technical Reference Manual, Version 2.0, Minolta, Inc., Japan, the disclosure of which is herein incorporated by reference.

Prior to measuring the reflective color of the beads, the Chroma Meter was color corrected on a standard white plate. Thereafter, control and treated polymer beads were placed in a small plastic weigh boat on the standard white plate in such a way that a layer, two beads thick, could be maintained. The Chroma Meter was placed in intimate contact with the beads and three readings were taken per sample in different locations on the beads. Mean values of L, a and b color space were obtained using the internal statistic capability of the unit.

Color difference between the control and treated beads was calculated as $\Delta E^*_{ab}$ using the following formula:

$$\Delta E^*_{ab} = \sqrt{(\Delta L^*)^2 + (\Delta a^*)^2 + (\Delta b^*)^2}$$

where, L* is the lightness factor (L=0 is black; L=100 is white), and a* and b* are chromaticity coordinates (+a=red; -a=green; +b=yellow; and -b=blue). Total color difference $\Delta E$ is defined by the geometric mean of the differences in the L, a, and b color coordinates between the control and treated polymer beads. The color chromatic coordinates (L, a and b) for the control beads and sample beads of Examples 1, and 5-10, and Comparative Examples 2-4, and 11-13, as well as the color difference ($\Delta E$) between the control and sample beads are shown below in Table 3.

A further analysis was performed on the rose bengal dye-impregnated PE beads of Example 9 to determine the amount of dye incorporated therein. Several grams of these beads were placed in 50 ml deionized water and stirred for 48 hours to extract the dye from the PE beads. A spectroscopic analysis was performed on the dye solution using a Perkin-Elmer, Lambda 4B, uv-vis spectrometer (Perkin-Elmer, Wilton, Conn.) at a wavelength of 356 nm. The results were compared to a standard curve for rose bengal dye. Spectroscopic analysis of the solution confirmed that approximately 0.04 mg of dye per gram of the polyethylene beads had been incorporated into the polyethylene beads during the impregnation process.

TABLE 2

Selected combinations of polymer material, impregnation additive, carrier medium (if any), supercritical fluid, including temperature and pressures utilized, method of sample treatment, and observed color change (if any), for Examples 1 and 5-10, and Comparative Examples 2-4, and 11-13.

| Ex. No. | Polymer Material | Impreg. Additive | Carrier Medium | SC Fluid | Temp (°C.) | Press. (MPa) | Sample Treatment | Observation |
|---|---|---|---|---|---|---|---|---|
| Ex. 1 | PE beads | rose bengal dye | water | $CO_2$ | 60 | 13.8 | PE beads immersed in solution of rose bengal dye and water | PE beads dyed dark pink throughout |
| C. Ex. 2 | PE beads | rose bengal dye | none | $CO_2$ | 60 | 13.8 | PE beads in first vial, dry rose bengal in second vial | PE beads remain milky white in color |
| C. Ex. 3 | PE beads | rose bengal dye | water | $CO_2$ | 60 | 13.8 | PE beads in first vial, sol. of rose bengal and water in second vial | PE beads remain milky white in color |
| C. Ex. 4 | PE beads | rose bengal dye | none | $CO_2$ | 60 | 13.8 | PE beads in vial with dry rose bengal dye | PE beads remain milky white in color |
| Ex. 5 | PP beads | rose bengal dye | water | $CO_2$ | 60 | 13.8 | PP beads immersed in solution of rose bengal and water | PP beads dyed pink throughout |
| Ex. 6 | PA pellets | rose bengal dye | water | $CO_2$ | 60 | 13.8 | PA pellets immersed in solution of rose bengal and water | PE beads dyed light pink throughout |
| Ex. 7 | PE beads | rose bengal dye | ETOH | $CO_2$ | 60 | 13.8 | PE beads immersed in solution of rose bengal and ETOH | PE beads light pink, not in bead center |
| Ex. 8 | PE beads | rose bengal dye | hexane | $CO_2$ | 60 | 13.8 | PE beads immersed in dispersion of rose bengal and hexane | PE beads dyed pink thoughout |
| Ex. 9 | PE beads | rose bengal dye | water | $CO_2$ | 35 | 13.8 | PE beads immersed in solution of rose bengal dye and water | PE beads dyed pink throughout |
| Ex. 10 | PE beads | rose bengal dye | water vapor | $CO_2$ | 60 | 13.8 | PE beads in vial with dry rose bengal, water in bottom of pressure vessel | PE beads remain milky white in color |
| C. Ex. 11 | PE beads | rose bengal dye | water | $CO_2$@ | 60 | 1.3 | PE beads immersed in solution in rose bengal and water | PE beads dyed very light pink |
| C. Ex. 12 | PE beads | rose bengal dye | water | $N_2$@ | 60 | 13.8 | PE beads immersed in solution of rose bengal and water | PE beads remain milky white in color |
| C. Ex. 13 | PE | rose | ETOH | $CO_2$ | 60 | 13.8 | PE beads in first vial, sol. of rose | PE beads remain |

TABLE 2-continued

Selected combinations of polymer material, impregnation additive, carrier medium (if any), supercritical fluid, including temperature and pressures utilized, method of sample treatment, and observed color change (if any), for Examples 1 and 5-10, and Comparative Examples 2-4, and 11-13.

| Ex. No. | Polymer Material | Impreg. Additive | Carrier Medium | SC Fluid | Temp (°C.) | Press. (MPa) | Sample Treatment | Observation |
| --- | --- | --- | --- | --- | --- | --- | --- | --- |
| | beads | bengal dye | | | | | bengal and ETOH in second vial | milky white in color |

@1.3 MPa comprises subcritical pressure conditions for $CO_2$, and 13.8 MPa comprises subcritical pressure conditions for $N_2$.

TABLE 3

Color chromatic coordinates (L, a and b) for the control beads and sample beads of Examples 1, and 5-10, and Comparative Examples 2-4, and 11-13, and color difference (ΔE) between the control and sample beads.

| Controls and Example Nos. | L | a | b | ΔE |
| --- | --- | --- | --- | --- |
| Polyethylene Control | 68.82 | −0.52 | +0.84 | |
| Example 1 | 53.52 | +24.22 | −9.58 | 30.90 |
| Comparative Example 2 | 75.58 | +0.73 | −0.97 | 7.10 |
| Comparative Example 3 | 72.95 | +1.66 | −1.61 | 5.27 |
| Comparative Example 4 | 70.28 | +6.90 | −2.84 | 8.41 |
| Polypropylene Control | 70.28 | −1.42 | +6.52 | |
| Example 5 | 53.85 | +18.44 | −3.18 | 27.54 |
| Polyamide Control | 52.74 | −1.14 | +29.35 | |
| Example 6 | 30.16 | +32.22 | +9.56 | 45.10 |
| Example 7 | 68.75 | +3.22 | −1.00 | 4.17 |
| Example 8 | 66.77 | +14.11 | −7.61 | 17.12 |
| Example 9 | na | na | na | na |
| Example 10 | 51.69 | +28.05 | −10.17 | 35.08 |
| Comparative Example 11 | 51.83 | +12.82 | −5.19 | 22.43 |
| Comparative Example 12 | 63.33 | +4.05 | −4.25 | 8.18 |
| Comparative Example 13 | 73.99 | +1.81 | −1.59 | 6.67 |

Comparative examples 2-4 show that rose bengal dye, whether separate or in contact, dry or in solution with water separate from the PE beads, does not impregnate the PE beads, and thus is insoluble in supercritical $CO_2$ at the disclosed conditions. Only by practicing the method of the present invention in Example 1, by simultaneously contacting the PE beads with an aqueous solution of rose bengal dye, is impregnation of the beads accomplished. In addition, Examples 5-9 illustrate that the same or similar results can be achieved with other polymers (PP and PA), other carrier liquids (ETOH and hexane), and at different temperature conditions (Example 1=60° C.; Example 9=35° C.). Example 10 shows that impregnation can be accomplished via a carrier liquid in a vapor (e.g., humid $H_2O$) rather than a liquid state. However, in such an instance the degree Of Visible dye impregnation is considerably lower than that accomplished using the carrier liquid in a liquid state (compare Examples 1 and 10).

Comparative Example 11 shows that some, albeit a significantly lesser degree of dye impregnation, can be accomplished using subcritical $CO_2$ (e.g., 1.3 MPa-v-13.8 MPa). However, use of subcritical $N_2$ does not result in dye impregnation. See Comparative Example 12. Furthermore, Comparative Example 13 confirms the result of Comparative Example 3, except using ETOH versus water as the carrier liquid.

The color measurements provided in Table 3 provide further quantification of the subjective observations of degree of dye impregnation noted in Table 2. Examples 1, 5, 6, and 10 using the preferred method of the present invention show the most pronounced darkening of the sample beads (i.e., reduced L value), the greatest increase in red coloration (greatest +a values), and largest overall color different (ΔE) relative to the control samples. In contrast, the coloration of Comparative Examples 2-4 show little or no significant difference in coloration from the controls. In this regard, the human eye can at beet detect a visible color difference of +5 units. In addition, the values for Examples 7 and 8 show that ETOH and hexane are not as effective carrier liquids as water (Compare to Example 1).

EXAMPLE 14

Four grams polyamide pellets (No. 19, 105-1, 3 mm diameter, melt index=95° C., Aldrich Chemical Co.) were placed in each of two separate 12 cc glass vials. A blue dye solution of 0.0437 g indigo carmine dye (Aldrich Chemical Co.) in 10 ml deionized water was placed in one vial, and a red dye solution of 0.0755 g rose bengal dye (Aldrich Chemical Co.) in 10 ml deionized water was placed in the second vial. Each vial was covered with a plug of glass wool to maintain the polyamide pellets immersed in the dye solutions. The vials were stacked in a 180 cc MICRO SERIES ™ pressure vessel (Newport Scientific Inc.), and the pressure vessel sealed. The vessel was charged with $CO_2$, stabilized at 13.8 MPa and 60° C., and maintained at these conditions for 17 hours. The vessel was slowly vented over a 15 minute period and the sample pellets recovered. Some of the polyamide pellets in the indigo carmine solution were floating, and showed visible blue dye impregnation where they were submerged in the dye solution, and no dye impregnation where they had floated above the dye solution. The polyamide pellets in the rose bengal dye solution remained completely submerged, and showed complete pink dye impregnation. There was no evidence of cross-contamination between the vials containing the dye solutions, as the dye solutions retained their original blue and rose tints, which in turn demonstrated insolubility of the dyes and dye solutions in supercritical $CO_2$ at the indicated temperature and pressure conditions.

The unimpregnated dyes were recovered from the solutions via rotary evaporation (recovered rose bengal dye=0.0636 g or 84%; recovered indigo carmine dye=0.0380 g or 87%). Thus, the impregnated polyamide pellets contained approximately 16% rose bengal dye, and 13% indigo carmine dye respectively, assuming negligible loss of dye during impregnation.

EXAMPLE 15

Five grams of polyamide pellets (No. 19,105-1; 3 mm diameter; melt index=95° C.; Aldrich Chemical Co.), five grams of polyethylene beads (ASPEN ™ No. 6806; 3 mm diameter; melt index =105° C.; linear low density polyethylene, Dow Chemical Co.) and an approximately 2.5 cm×2.5 cm×1 mm thick polyurethane film (source unknown) were placed in a single glass vial containing a dye solution of 50 ml deionized water, 13 mg rose bengal dye (Aldrich Chemical Co.) and 2 drops of an aqueous solution of FD&C blue dye No. 1 (Schilling Food Color; McCormick & Co., Hunt Valley, Md.). A glass wool plug was used to keep the polymer samples submerged in the dye solution. The vial was placed in a 180 cc MICRO SERIES ™ pressure vessel, which was sealed, charged with carbon dioxide, stabilized at 50° C. and 13.8 MPa, and maintained for 17 hours. Thereafter, the vessel was vented down over a 1 minute period, and the polymer samples and dye solution recovered. Each of the polymer samples were rinsed with two portions of deionized water and blotted dry. The polyurethane film was removed, and the polyamide pellets and polyethylene beads were separated from one another by shape differentiation. All polymer samples were colored bluish-rose indicating impregnation by both dyes therein.

Each of the three polymer samples were placed in a beaker containing 20 mils of a pH 9 aqueous buffer solution (Fisher Scientific Co., Fairlawn, N.J.), and stirred overnight. Each of the aqueous buffer solutions were qualitatively analyzed in a Perkin-Elmer, Lambda 4B, uv-vis spectrometer (Perkin-Elmer, Wilton, Conn.) at wavelengths of 514 nm and 550 nm. Both the buffer solutions containing the polyamide pellets and the polyethylene beads contained partially extracted dyes, which when analyzed chowed absorbencies at 514 nm and 550 nm for the FD&C blue dye No. 1, and rose bengal dye, respectively. The buffer solution containing the polyurethane film sample did not contain any extracted dyes.

EXAMPLE 16

Five grams polyethylene beads (ASPEN TM No. 6806; 3 mm diameter; melt index=105° C.; linear low density polyethylene, Dow Chemical Co.), a 25 cm×25 cm×1 mm thick polyurethane (PU) and polyethylene terephthalite (PET) laminated film (source unknown), and an approximately 3.5 cm×3.5 cm×1 mm thick silicone film (SILASTIC TM No., Dow Corning corp., midland, Mich.) were placed in a 25 cc glass vial containing 0.25 g robe bengal dye (Aldrich Chemical Co.) dissolved in 25 mls of absolute ethyl alcohol (ETOH). The vial was placed in a 300 cc pressure vessel. In addition, 30 mils ETOH was also placed in the bottom of the pressure vessel, outside the glass vial, to create a saturated ETOH/supercritical $CO_2$ solution, and thereby prevent the complete uptake of the ethanol f rom the sample vial, when the pressure vessel was pressurized.

After placement of the vial and excess ETOH, the pressure vessel was closed, charged with $CO_2$, stabilized at 20.7 MPa and 40° C., and maintained for 4 hours. Thereafter, the pressure vessel was vented down over a 2 minute period, and the polymer samples recovered and rinsed with deionized water. The polyethylene beads were pink, and the silicone film was red, indicating impregnation by the rose bengal dye. In addition, the polyurethane side of the PU/PET film was red, indicating dye impregnation, but the PET layer on the opposite side of the film laminate remained clear. Thus, the disclosed impregnations conditions were sufficient to provide impregnation of all but the PET polymer. In this regard, the PET would probably require more rigorous temperature and pressure conditions to provide for impregnation of the rose bengal dye therein.

COMPARATIVE EXAMPLE 17

Two pieces of polyvinyl chloride (PVC) tubing (TYGON TM tubing; Norton Co., Worcester, Mass.), which contain a plasticizing agent were weighed. The first sample weighed 2.0732 grams and wall placed in a test tube without water. The second sample weighed 2.1546 grams and was placed in a test tube containing a solution of 0.1050 g of indigo carmine dye (Aldrich Chemical Co.) in 20 ml of deionized water. Both test tubes were placed in a pressure vessel, which was sealed, charged with $CO_2$, stabilized at 20.7 MPa and 50° C., and maintained for 5 hours. Thereafter, the pressure vessel was rapidly vented down to atmospheric pressure, and the samples were recovered.

The first sample of PVC tubing exposed directly to supercritical $CO_2$ foamed, visibly shrank in size, became very stiff, and lost 0.4307 grams, or approximately 20 percent of its total weight. In addition, the test tube containing the first sample also contained a small portion of an oily liquid, assumed to contain extracted plasticizer, based on the stiff physical characteristics of the foamed tubing.

The second sample of PVC tubing immersed in the indigo carmine dye solution retained its soft, pliable character, and foamed due to the rapid venting of the pressure vessel. The final weight of the second sample was 2.0770 grams, a slight increase of 3.8 mg, most likely due to absorption of moisture into the foamed tubing. In addition, none of the oily substance observed with the first sample was observed on the tubing, or in the dye test tube containing the dye solution. Furthermore, no impregnation of the indigo carmine dye was observed in the second sample of foamed tubing.

This example shows that the method of the present invention does not lead to unwanted extraction of additives from the polymer to be impregnated, as is observed when utilizing the prior art method. In addition, while dye impregnation was not accomplished under the disclosed conditions, it may be reasonably assumed that more rigorous temperature and/or pressure conditions could result in the impregnation of indigo carmine dye into the PVC tubing. Furthermore, through more selective control of the venting of the pressure vessel (i.e. more slowly), foaming of the PVC tubing could be prevented.

While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A method of impregnating a polymeric substrate with an impregnation additive comprising:
    (a) placing a polymeric substrate into a pressure vessel at atmospheric pressure;
    (b) simultaneously contacting the polymeric substrate with a mixture of a carrier liquid and an impregnation additive, wherein the impregnation additive is substantially insoluble in a supercritical fluid;
    (c) sealing the pressure vessel;
    (d) exposing the polymeric substrate and the mixture of the carrier liquid and impregnation additive to the supercritical fluid in the pressure vessel for time sufficient to swell the polymeric substrate, such that the carrier liquid and impregnation additive at least partially penetrates the swollen polymeric substrate; and
    (e) releasing the pressure in the pressure vessel so that the carrier liquid diffuses out of the swollen polymeric substrate, wherein an amount of the impregnation additive is entrapped within the polymeric substrate.

2. A method of impregnating a polymeric material according to claim 1, wherein the supercritical fluid comprises supercritical carbon dioxide.

3. A method of impregnating a polymeric material according to claim 1, wherein the polymeric material is selected from the group consisting of polyolefin polymers, polyamide polymers, polyurethane polymers, silicone polymers, protein derivative polymers, lactic acid polymers, glycolic acid polymers, and combinations thereof.

4. A method of impregnating a polymeric material according to claim 3, wherein the polyolefin polymer is selected from the group consisting of a low density polyethylene, linear low density polyethylene, polypropylene, and combinations thereof.

5. A method of impregnating a polymeric material according to claim 1, wherein the carrier liquid is selected from the group consisting of water, methanol, ethanol, isopropanol, hexane, and combinations thereof.

6. A method of impregnating a polymeric material according to claim 1, wherein the carrier liquid is substantially insoluble in the supercritical fluid.

7. A method of impregnating a polymeric material according to claim 1, wherein the carrier liquid is substantially insoluble in the polymeric material.

8. A method of impregnating a polymeric material according to claim 1, wherein the impregnation additive is substantially insoluble in the polymeric material.

9. A method of impregnating a polymeric material according to claim 1, wherein the impregnation additive is selected from the group consisting of a dye, a protein, a polypeptide, a nucleotide, a drug, a monomer, and combinations thereof.

10. A method of impregnating a polymeric substrate with an impregnation additive comprising;
 (a) placing a polymeric substrate into a pressure vessel at atmospheric pressure;
 (b) simultaneously contacting the polymeric substrate with a mixture of a carrier liquid and an impregnation additive, wherein the impregnation additive is substantially insoluble in a supercritical fluid and comprises a dye selected from the group consisting of fluorescein dyes, indigo dyes, and combinations thereof;
 (c) sealing the pressure vessel;
 (d) exposing the polymeric substrate and the mixture of the carrier liquid and impregnation additive to the supercritical fluid in the pressure vessel for time sufficient to swell the polymeric substrate, such that the carrier liquid and impregnation additive at least partially penetrates the swollen polymeric substrate; and
 (e) releasing the pressure in the pressure vessel so that the carrier liquid diffuses out of the swollen polymeric substrate, wherein an amount of the impregnation additive is entrapped within the polymeric substrate.

11. A method of impregnating a polymeric material according to claim 9, wherein the impregnation additive comprises a drug selected from the group consisting of antibiotics, antiinflammatory agents, cardiovascular agents, analgesics, calcium channel blockers, beta-blockers, antidepressants, antacids, antidiabetics, cerebral stimulants, sedatives, anti-parasitics, decongestants, muscle relaxants, anti-Parkinsonism agents, antiviral agents, bronchodialators, vitamins, dietary supplements, and combinations thereof.

12. A method of impregnating a polymeric substrate with a hydrophilic impregnation additive comprising:
 (a) placing a polymeric substrate into a pressure vessel at atmospheric pressure;
 (b) simultaneously contacting the polymeric substrate with a mixture of a carrier liquid and a hydrophilic impregnation additive;
 (c) sealing the pressure vessel;
 (d) exposing the polymeric substrate and the mixture of the carrier liquid and hydrophilic impregnation additive to a lipophilic supercritical fluid in the pressure vessel for time sufficient to swell the polymeric substrate, such that the carrier liquid and hydrophilic impregnation additive at least partially penetrates the swollen polymeric substrate; and
 (e) releasing the pressure in the pressure vessel so that the carrier liquid diffuses out of the swollen polymeric substrate, wherein an amount of the hydrophilic impregnation additive is entrapped within the polymeric substrate.

13. A method of impregnating a polymeric material according to claim 12, wherein the carrier liquid comprises water.

14. A method of impregnating a polymeric material according to claim 12, wherein the lipophilic supercritical fluid comprises supercritical carbon dioxide.

15. A method of impregnating a polymeric material according to claim 12, wherein the polymeric material is selected from the group consisting of polyolefin polymers, polyamide polymers, polyurethane polymers, silicone polymers, protein derivative polymers, lactic acid polymers, glycolic acid polymers, and combinations thereof.

16. A method of impregnating a polymeric material according to claim 12, wherein the carrier liquid is substantially insoluble in the lipophilic supercritical fluid.

17. A method of impregnating a polymeric material according to claim 12, wherein the carrier liquid is substantially insoluble in the polymeric material.

18. A method of impregnating a polymeric material according to claim 12, wherein the impregnation additive is substantially insoluble in the polymeric material.

19. A method of impregnating a polymeric material according to claim 12, wherein the impregnation additive is selected from the group consisting of a dye, a protein, a polypeptide, a nucleotide, a drug, a monomer, and combinations thereof.

* * * * *

UNITED STATES PATENT AND TRADEMARK OFFICE
CERTIFICATE OF CORRECTION

PATENT NO. : 5,340,614
DATED : August 23, 1994
INVENTOR(S) : Perman et al.

It is certified that error appears in the above-indentified patent and that said Letters Patent is hereby corrected as shown below:

Col. 1, line 65, Replace "Bolvent" with --solvent--

Col. 5, line 24, Replace "bata" with --Data--

Col. 5, line 65, Replace "Preferred" with --preferred--

Col. 6, line 3, Replace "PC" with --$P_c$--

Col. 6, line 15, Insert --As-- before "with"

Col. 7, line 53, Replace "Gaddings" with --Giddings--

Col. 9, line 6, Replace "COBT" with --cost--

Col. 9, line 41, Replace "cellulobe" with --cellulose--

Col. 13, line 27, Replace "Cr-231" with --CR-231--

Col. 13, line 27, Replace "tribtimulus" with --tristimulus--

Col. 15, line 45, Replace "Of Visible" with --of visible--

Col. 15, line 68, Replace "beet" with --best--

Col. 15, line 68, Replace "+5" with --±5--

Col. 17, line 21, Replace "chowed" with --showed--

UNITED STATES PATENT AND TRADEMARK OFFICE
CERTIFICATE OF CORRECTION

PATENT NO. : 5,340,614

DATED : August 23, 1994

INVENTOR(S) : Perman et al.

Page 2 of 2

It is certified that error appears in the above-indentified patent and that said Letters Patent is hereby corrected as shown below:

Col. 17, line 42, Replace "f rom" with --from--

Col. 17, line 65, Replace "wall" with --was--

Col. 20, line 4, "antiinflanunatory" should read --anti-inflammatory--.

Signed and Sealed this

Twenty-ninth Day of November, 1994

Attest:

BRUCE LEHMAN

*Attesting Officer*  *Commissioner of Patents and Trademarks*